US012773233B2

(12) United States Patent
Van Tol et al.

(10) Patent No.: US 12,773,233 B2
(45) Date of Patent: Oct. 27, 2026

(54) SURGICAL SYSTEMS AND METHODS LEVERAGING AN ULTRASONIC TRANSDUCER SATURATION POINT

(71) Applicant: Covidien LP, Mansfield, MA (US)

(72) Inventors: David J. Van Tol, Boulder, CO (US); Matthew S. Cowley, Frederick, CO (US); Keith W. Malang, Longmont, CO (US); Anthony B. Ross, Boulder, CO (US); Christopher A. Valentine, Longmont, CO (US); Aaron G. Mattmiller, Longmont, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 603 days.

(21) Appl. No.: 17/716,683

(22) Filed: Apr. 8, 2022

(65) Prior Publication Data

US 2022/0346826 A1 Nov. 3, 2022

Related U.S. Application Data

(60) Provisional application No. 63/183,266, filed on May 3, 2021.

(51) Int. Cl.
*A61B 17/32* (2006.01)

(52) U.S. Cl.
CPC ................. *A61B 17/320092* (2013.01); *A61B 2017/320069* (2017.08)

(58) Field of Classification Search
CPC .... A61B 17/320068; A61B 17/320092; A61B 2017/320093; A61B 2017/320094; A61B 2017/320095; A61B 2017/320069; A61B 2017/320089; A61B 2017/320071
See application file for complete search history.

(56) References Cited

U.S. PATENT DOCUMENTS

| | | | |
|---|---|---|---|
| 1,813,902 | A | 7/1931 | Bovie |
| 2,874,470 | A | 2/1959 | Richards |
| 2,990,616 | A | 7/1961 | Balamuth |
| 3,432,691 | A | 3/1969 | Shoh |
| 3,489,930 | A | 1/1970 | Shoh |
| 3,526,792 | A | 9/1970 | Shoh |
| 3,629,726 | A | 12/1971 | Popescu |
| 3,668,486 | A | 6/1972 | Silver |
| 3,809,977 | A | 5/1974 | Balamuth et al. |
| 3,875,945 | A | 4/1975 | Friedman |
| 3,924,335 | A | 12/1975 | Balamuth et al. |

(Continued)

*Primary Examiner* — Tan-Uyen T Ho
*Assistant Examiner* — Mohammed S Adam

(57) ABSTRACT

An ultrasonic surgical system includes an ultrasonic generator configured to provide an electrical drive signal, an ultrasonic transducer configured to receive the electrical drive signal and to produce ultrasonic mechanical motion in response thereto, and a blade coupled to the ultrasonic transducer and configured to receive the ultrasonic mechanical motion from the ultrasonic transducer for treating tissue in contact therewith. The ultrasonic transducer defines a saturation point and the ultrasonic generator is configured to drive the ultrasonic transducer substantially at the saturation point such that the ultrasonic mechanical motion produced by the ultrasonic transducer is substantially equal to a maximum ultrasonic mechanical motion of the ultrasonic transducer.

20 Claims, 10 Drawing Sheets

(56) References Cited

U.S. PATENT DOCUMENTS 4,012,647 A 3/1977 Balamuth et al.
4,193,818 A 3/1980 Young et al.
4,227,110 A 10/1980 Douglas et al.
4,300,083 A 11/1981 Heiges
4,302,728 A 11/1981 Nakamura
4,309,067 A 1/1982 Riley, Jr.
4,370,302 A 1/1983 Suzuoka et al.
4,641,053 A 2/1987 Takeda
4,903,696 A 2/1990 Stasz et al.
5,113,116 A 5/1992 Wilson
5,224,680 A 7/1993 Greenstein et al.
5,264,925 A 11/1993 Shipp et al.
5,275,166 A 1/1994 Vaitekunas et al.
5,374,813 A 12/1994 Shipp
5,394,187 A 2/1995 Shipp
5,408,268 A 4/1995 Shipp
5,451,220 A 9/1995 Ciervo
5,490,860 A 2/1996 Middle et al.
5,553,478 A 9/1996 Di Troia
5,565,520 A 10/1996 Fock et al.
5,582,617 A 12/1996 Klieman et al.
5,593,414 A 1/1997 Shipp et al.
5,600,230 A 2/1997 Dunstan
5,685,311 A 11/1997 Hara
5,717,306 A 2/1998 Shipp
5,728,130 A 3/1998 Ishikawa et al.
5,792,138 A 8/1998 Shipp
5,796,056 A 8/1998 Bredow et al.
5,810,859 A 9/1998 DiMatteo et al.
5,858,018 A 1/1999 Shipp et al.
5,873,873 A 2/1999 Smith et al.
5,897,569 A 4/1999 Kellogg et al.
5,910,152 A 6/1999 Bays
5,938,633 A 8/1999 Beaupre
5,944,737 A 8/1999 Tsonton et al.
5,947,984 A 9/1999 Whipple
5,949,213 A 9/1999 Lanni
5,954,736 A 9/1999 Bishop et al.
5,993,465 A 11/1999 Shipp et al.
5,994,855 A 11/1999 Lundell et al.
6,028,387 A 2/2000 Boukhny
6,031,526 A 2/2000 Shipp
6,036,667 A 3/2000 Manna et al.
6,068,647 A 5/2000 Witt et al.
6,095,981 A 8/2000 McGahan
6,162,194 A 12/2000 Shipp
6,183,426 B1 2/2001 Akisada et al.
6,220,098 B1 4/2001 Johnson et al.
6,220,368 B1 4/2001 Ark et al.
6,254,623 B1 7/2001 Haibel, Jr. et al.
6,257,241 B1 7/2001 Wampler
6,278,218 B1 8/2001 Madan et al.
6,280,407 B1 8/2001 Manna et al.
6,283,981 B1 9/2001 Beaupre
6,284,185 B1 9/2001 Tokuda et al.
6,287,344 B1 9/2001 Wampler et al.
6,290,575 B1 9/2001 Shipp
6,306,157 B1 10/2001 Shchervinsky
6,309,400 B2 10/2001 Beaupre
6,325,811 B1 12/2001 Messerly
6,328,751 B1 12/2001 Beaupre
6,346,795 B2 2/2002 Haraguchi et al.
6,350,269 B1 2/2002 Shipp et al.
6,352,532 B1 3/2002 Kramer et al.
6,416,486 B1 7/2002 Wampler
6,423,082 B1 7/2002 Houser et al.
6,432,118 B1 8/2002 Messerly
6,443,968 B1 9/2002 Holthaus et al.
6,449,006 B1 9/2002 Shipp
6,454,781 B1 9/2002 Witt et al.
6,454,782 B1 9/2002 Schwemberger
6,458,142 B1 10/2002 Faller et al.
6,480,796 B2 11/2002 Wiener
6,482,220 B1 11/2002 Mueller
6,491,708 B2 12/2002 Madan et al.
6,500,188 B2 12/2002 Harper et al.
6,514,267 B2 2/2003 Jewett
6,537,291 B2 3/2003 Friedman et al.
6,561,983 B2 5/2003 Cronin et al.
6,565,520 B1 5/2003 Young
6,588,277 B2 7/2003 Giordano et al.
6,589,200 B1 7/2003 Schwemberger et al.
6,607,540 B1 8/2003 Shipp
6,623,500 B1 9/2003 Cook et al.
6,626,890 B2 * 9/2003 Nguyen ......... A61B 17/320016 604/902
6,626,926 B2 9/2003 Friedman et al.
6,633,234 B2 10/2003 Wiener et al.
6,652,539 B2 11/2003 Shipp et al.
6,652,545 B2 11/2003 Shipp et al.
6,660,017 B2 12/2003 Beaupre
6,662,127 B2 12/2003 Wiener et al.
6,666,875 B1 12/2003 Sakurai et al.
6,678,621 B2 1/2004 Wiener et al.
6,679,899 B2 1/2004 Wiener et al.
6,719,776 B2 4/2004 Baxter et al.
6,752,815 B2 6/2004 Beaupre
6,773,444 B2 8/2004 Messerly
6,869,439 B2 3/2005 White et al.
6,908,472 B2 6/2005 Wiener et al.
6,915,623 B2 7/2005 Dey et al.
6,945,981 B2 9/2005 Donofrio et al.
6,976,969 B2 12/2005 Messerly
7,037,306 B2 5/2006 Podany et al.
7,066,895 B2 6/2006 Podany
7,074,218 B2 7/2006 Washington et al.
7,108,695 B2 9/2006 Witt et al.
7,128,720 B2 10/2006 Podany
7,135,030 B2 11/2006 Schwemberger et al.
7,163,548 B2 1/2007 Stulen et al.
7,179,254 B2 2/2007 Pendekanti et al.
7,179,271 B2 2/2007 Friedman et al.
7,207,997 B2 4/2007 Shipp et al.
7,217,128 B2 5/2007 Atkin et al.
7,217,893 B1 5/2007 Huang et al.
7,230,199 B2 6/2007 Chou et al.
7,244,262 B2 7/2007 Wiener et al.
7,269,873 B2 9/2007 Brewer et al.
7,273,483 B2 9/2007 Wiener et al.
7,300,446 B2 11/2007 Beaupre
7,335,997 B2 2/2008 Wiener
7,337,010 B2 2/2008 Howard et al.
7,977,587 B2 7/2011 Rajagopal et al.
9,017,355 B2 4/2015 Smith et al.
9,107,690 B2 8/2015 Bales, Jr. et al.
9,314,261 B2 4/2016 Bales, Jr. et al.
10,194,972 B2 2/2019 Yates et al.
10,194,973 B2 2/2019 Wiener et al.
10,265,117 B2 4/2019 Wiener et al.
10,321,950 B2 6/2019 Yates et al.
10,335,614 B2 7/2019 Messerly et al.
10,342,602 B2 7/2019 Strobl et al.
10,368,894 B2 8/2019 Madan et al.
10,376,305 B2 8/2019 Yates et al.
10,420,579 B2 9/2019 Wiener et al.
10,537,394 B2 1/2020 Strobl
10,537,399 B2 1/2020 Eckert et al.
10,624,667 B2 4/2020 Faller et al.
10,639,059 B2 5/2020 Groene et al.
10,653,437 B2 5/2020 Dannaher et al.
10,687,884 B2 6/2020 Wiener et al.
10,736,685 B2 8/2020 Wiener et al.
10,751,108 B2 8/2020 Yates et al.
10,799,913 B2 10/2020 Bales, Jr. et al.
10,813,703 B2 10/2020 Swayze et al.
10,898,256 B2 1/2021 Yates et al.
10,912,580 B2 2/2021 Green et al.
10,952,788 B2 3/2021 Asher et al.
11,033,292 B2 6/2021 Green et al.
11,058,475 B2 7/2021 Wiener et al.
2002/0002379 A1 1/2002 Bishop
2002/0077645 A1 6/2002 Wiener et al.
2002/0091339 A1 7/2002 Horzewski et al.
2002/0138090 A1 9/2002 Jewett

(56) References Cited

U.S. PATENT DOCUMENTS

2003/0144680 A1 7/2003 Kellogg et al.
2003/0149424 A1 8/2003 Barlev et al.
2003/0199794 A1 10/2003 Sakurai et al.
2003/0212363 A1 11/2003 Shipp
2004/0054364 A1* 3/2004 Aranyi .......... A61B 17/320068 606/27
2004/0097972 A1 5/2004 Shipp et al.
2004/0116952 A1 6/2004 Sakurai et al.
2004/0256487 A1 12/2004 Collins et al.
2005/0033201 A1 2/2005 Takahashi et al.
2005/0091770 A1 5/2005 Mourad et al.
2005/0107658 A1 5/2005 Brockway
2005/0113815 A1 5/2005 Ritchie et al.
2005/0119677 A1 6/2005 Shipp
2005/0149063 A1 7/2005 Young et al.
2005/0159752 A1 7/2005 Walker et al.
2005/0203329 A1 9/2005 Muto et al.
2005/0234338 A1 10/2005 Masuda
2005/0234484 A1 10/2005 Houser et al.
2006/0058825 A1 3/2006 Ogura et al.
2006/0076934 A1 4/2006 Ogata et al.
2006/0079878 A1 4/2006 Houser
2006/0079879 A1 4/2006 Faller et al.
2006/0087286 A1 4/2006 Phillips et al.
2006/0129168 A1 6/2006 Shipp
2006/0178579 A1 8/2006 Haynes
2006/0178667 A1 8/2006 Sartor et al.
2006/0194567 A1 8/2006 Kelly et al.
2006/0206100 A1 9/2006 Eskridge et al.
2006/0217729 A1 9/2006 Eskridge et al.
2006/0220613 A1 10/2006 Abe
2007/0011836 A1 1/2007 Brewer et al.
2007/0149881 A1 6/2007 Rabin
2007/0166663 A1 7/2007 Telles et al.
2007/0175960 A1 8/2007 Shelton et al.
2007/0227866 A1 10/2007 Dimig
2007/0239028 A1 10/2007 Houser et al.
2007/0239101 A1 10/2007 Kellogg
2008/0033248 A1 2/2008 Akagi
2008/0051693 A1 2/2008 Babaev
2008/0215056 A1 9/2008 Miller et al.
2008/0245841 A1 10/2008 Smith et al.
2008/0251568 A1 10/2008 Zemlok et al.
2009/0066192 A1* 3/2009 Taki .................... G10K 11/004 310/354
2009/0138006 A1 5/2009 Bales et al.
2009/0143797 A1 6/2009 Smith et al.
2009/0143805 A1 6/2009 Palmer et al.
2009/0223033 A1 9/2009 Houser
2010/0000074 A1 1/2010 Smith et al.
2010/0004669 A1 1/2010 Smith et al.
2010/0125292 A1* 5/2010 Wiener .......... A61B 17/320068 606/169
2011/0009890 A1 1/2011 Palmer et al.
2011/0024479 A1 2/2011 Swensgard et al.
2011/0087256 A1 4/2011 Wiener et al.
2012/0078278 A1 3/2012 Bales, Jr. et al.
2013/0267975 A1 10/2013 Timm et al.
2013/0282003 A1 10/2013 Messerly
2015/0157354 A1 6/2015 Bales, Jr.
2017/0332909 A1 11/2017 Nagae
2019/0216530 A1* 7/2019 Kabala ............... A61B 18/1445

* cited by examiner

SURGICAL SYSTEMS AND METHODS LEVERAGING AN ULTRASONIC TRANSDUCER SATURATION POINT

CROSS-REFERENCE TO RELATED APPLICATIONS

This application claims the benefit of, and priority to, U.S. Provisional Patent Application No. 63/183,266, filed on May 3, 2021, the entire contents of which are hereby incorporated herein by reference.

FIELD

The present disclosure relates to surgical systems and methods, and, more particularly, to surgical systems and methods leveraging an ultrasonic transducer saturation point to facilitate, for example, design, feedback, and/or control of ultrasonic transducers and/or surgical systems.

BACKGROUND

Surgical instruments and systems incorporating ultrasonic functionality utilize ultrasonic energy, i.e., ultrasonic vibrations, to treat tissue. More specifically, mechanical vibration energy transmitted at ultrasonic frequencies can be utilized to treat, e.g., seal and transect, tissue. A surgical instrument incorporating ultrasonic functionality may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

SUMMARY

As used herein, the term “distal” refers to the portion that is described which is further from an operator (whether a human surgeon or a surgical robot), while the term “proximal” refers to the portion that is being described which is closer to the operator. Terms including “generally,” “about,” “substantially,” and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is an ultrasonic surgical system including an ultrasonic generator configured to provide an electrical drive signal, an ultrasonic transducer configured to receive the electrical drive signal and to produce ultrasonic mechanical motion in response thereto, and a blade coupled to the ultrasonic transducer and configured to receive the ultrasonic mechanical motion from the ultrasonic transducer for treating tissue in contact therewith. The ultrasonic transducer defines a saturation point and the ultrasonic generator is configured to drive the ultrasonic transducer substantially at the saturation point such that the ultrasonic mechanical motion produced by the ultrasonic transducer is substantially equal to a maximum ultrasonic mechanical motion of the ultrasonic transducer.

In an aspect of the present disclosure, the system further includes a housing and an elongated assembly extending distally from the housing. The blade is positioned at a distal end portion of the elongated assembly.

In another aspect of the present disclosure, the ultrasonic transducer is supported on or within the housing. Alternatively or additionally, the ultrasonic generator is supported on or within the housing.

In still another aspect of the present disclosure, the ultrasonic transducer is supported within the elongated assembly at a position distally-spaced from the housing. In such aspects, the elongated assembly may be configured to articulate about at least one articulation joint and the ultrasonic transducer may be positioned distally of the at least one articulation joint.

In yet another aspect of the present disclosure, an ultrasonic waveguide interconnects the ultrasonic transducer with the blade.

In still yet another aspect of the present disclosure, the system further includes a jaw member movable relative to the blade between a spaced-apart position and an approximated position for clamping tissue therebetween. In such aspects, at least one of the jaw member or the blade may be configured to connect to a source of electrosurgical energy for communicating electrosurgical energy to tissue clamped between the blade and the jaw member.

Another ultrasonic surgical system provided in accordance with aspects of the present disclosure includes an ultrasonic transducer and a blade coupled to the ultrasonic transducer. The ultrasonic transducer defines a saturation point and is configured, in response to receiving an electrical drive signal to drive the ultrasonic transducer at substantially the saturation point, to produce a maximum ultrasonic mechanical motion. The blade is configured to receive the maximum ultrasonic mechanical motion from the ultrasonic transducer. The ultrasonic transducer is configured such that the maximum ultrasonic mechanical motion moves the blade at a velocity of at least 8 m/s Root Mean Square (RMS) for treating tissue in contact therewith.

In an aspect of the present disclosure, the system further includes an ultrasonic generator configured to provide the electrical drive signal to the ultrasonic transducer.

In another aspect of the present disclosure, the system further includes a housing and an elongated assembly extending distally from the housing. The blade, in such aspects, is positioned at a distal end portion of the elongated assembly.

In still another aspect of the present disclosure, the ultrasonic transducer is supported within the elongated assembly at a position distally-spaced from the housing. The elongated assembly, in such aspects, may be configured to articulate about at least one articulation joint and the ultrasonic transducer may be positioned distally of the at least one articulation joint.

In aspects of the present disclosure, a maximum outer diameter of the ultrasonic transducer is no greater than about 8 mm or, in aspects, no greater than about 6 mm. Additionally or alternatively, the maximum ultrasonic mechanical motion moves the blade at an oscillating velocity of at least 10 m/s RMS for treating tissue in contact therewith.

In still yet another aspect of the present disclosure, the system further includes a jaw member movable relative to the blade between a spaced-apart position and an approximated position for clamping tissue therebetween. In such aspects, at least one of the jaw member or the blade may be configured to connect to a source of electrosurgical energy for communicating electrosurgical energy to tissue clamped between the blade and the jaw member.

A method of operating an ultrasonic surgical system provided in accordance with aspects of the present disclosure includes determining a saturation point of an ultrasonic transducer, determining an electrical drive signal to drive the ultrasonic transducer substantially at the saturation point, and providing the electrical drive signal to the ultrasonic transducer such that the ultrasonic transducer produces a maximum ultrasonic mechanical motion for transmission to a blade coupled to the ultrasonic transducer for treating tissue in contact therewith.

In aspects of the present disclosure, the method further includes controlling the electrical drive signal to maintain the ultrasonic transducer substantially at the saturation point.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
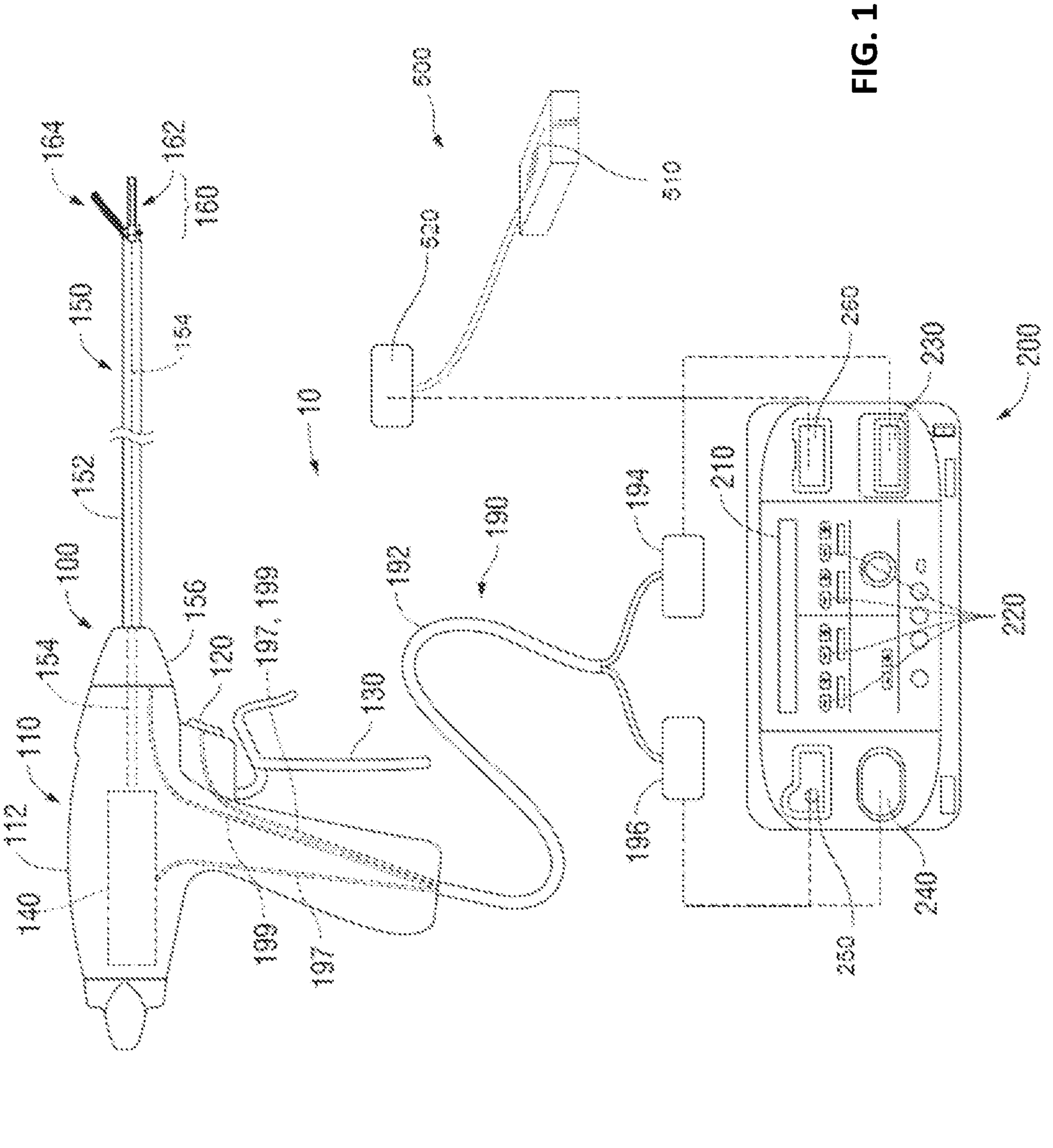
FIG. 1 is a side view of a surgical system provided in accordance with the present disclosure including a surgical instrument, a surgical generator, and a return electrode device.

Referring to FIG. 1, a surgical system provided in accordance with aspects of the present disclosure is shown generally identified by reference numeral 10 including a surgical instrument 100, a surgical generator 200, and, in some aspects, a return electrode device 500, e.g., including a return pad 510. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200.

Surgical generator 200 includes a display 210, a plurality user interface features 220, e.g., buttons, touch screens, switches, etc., an ultrasonic plug port 230, a bipolar electrosurgical plug port 240, and active and return monopolar electrosurgical plug ports 250, 260, respectively. As an alternative to plural dedicated ports 230-260, one or more common ports (not shown) may be configured to act as any two or more of ports 230-260.

Surgical instrument 100 is configured to operate in one or more electrosurgical modes supplying Radio Frequency (RF) energy to tissue to treat tissue, e.g., a monopolar configuration and/or a bipolar configuration, and an ultrasonic mode supplying ultrasonic energy to tissue to treat tissue. Surgical generator 200 is configured to produce ultrasonic drive signals for output through ultrasonic plug port 230 to surgical instrument 100 to activate surgical instrument 100 in the ultrasonic mode and to provide electrosurgical energy, e.g., RF bipolar energy for output through bipolar electrosurgical plug port 240 and/or RF monopolar energy for output through active monopolar electrosurgical port 250 to surgical instrument 100 to activate surgical instrument 100 in the one or more electrosurgical modes. Plug 520 of return electrode device 500 is configured to connect to return monopolar electrosurgical plug port 260 to return monopolar electrosurgical energy from surgical instrument 100 in the monopolar electrosurgical mode. In other aspects, the electrosurgical functionality (and associated components and configurations) of surgical instrument 100 may be omitted such that surgical instrument 100 operates only in an ultrasonic mode.

Continuing with reference to FIG. 1, handle assembly 110 includes a housing 112, an activation button 120, and a clamp trigger 130. Housing 112 is configured to support an ultrasonic transducer 140. Ultrasonic transducer 140 may be permanently engaged within housing 112 or removable therefrom. Ultrasonic transducer 140 includes a piezoelectric stack other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. Feedback and/or control signals may likewise be communicated between ultrasonic transducer 140 and surgical generator 200. Ultrasonic transducer 140, more specifically, may include a stack of piezoelectric elements secured, under pre-compression between proximal and distal end masses or a proximal end mass and an ultrasonic horn with first and second electrodes electrically coupled between piezoelectric elements of the stack of piezoelectric elements to enable energization thereof to produce ultrasonic energy. However, other suitable ultrasonic transducer configurations, including plural transducers and/or non-linear, e.g., torsional, transducers are also contemplated.

An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting (such as a LOW power or tissue sealing setting) and a second actuated position corresponding to a second activation setting (such as a HIGH power or tissue transection setting). In still other configurations, separate activation buttons may be provided, e.g., a first actuation button for activating a first activation setting and a second activation button for activating a second activation setting. Additional activation buttons, sliders, wheels, etc. are also contemplated to enable control of various different activation settings from housing 112.

Elongated assembly 150 of surgical instrument 100 includes an outer drive sleeve 152, an inner support sleeve 153 (FIG. 5) disposed within outer drive sleeve 152, a waveguide 154 extending through inner support sleeve 153 (FIG. 5), a drive assembly (not shown), a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164 and a distal end of inner support sleeve 153 (FIG. 5) pivotably supports jaw member 164. As such, clamp trigger 130 is selectively actuatable to thereby move outer drive sleeve 152 about inner support sleeve 153 (FIG. 5) to pivot jaw member 164 relative to blade 162 of end effector assembly 160 from a spaced apart position to an approximated position for clamping tissue between jaw member 164 and blade 162. The configuration of outer and inner sleeves 152, 153 (FIG. 5) may be reversed, e.g., wherein outer sleeve 152 is the support sleeve and inner sleeve 153 (FIG. 5) is the drive sleeve. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Figure 5:
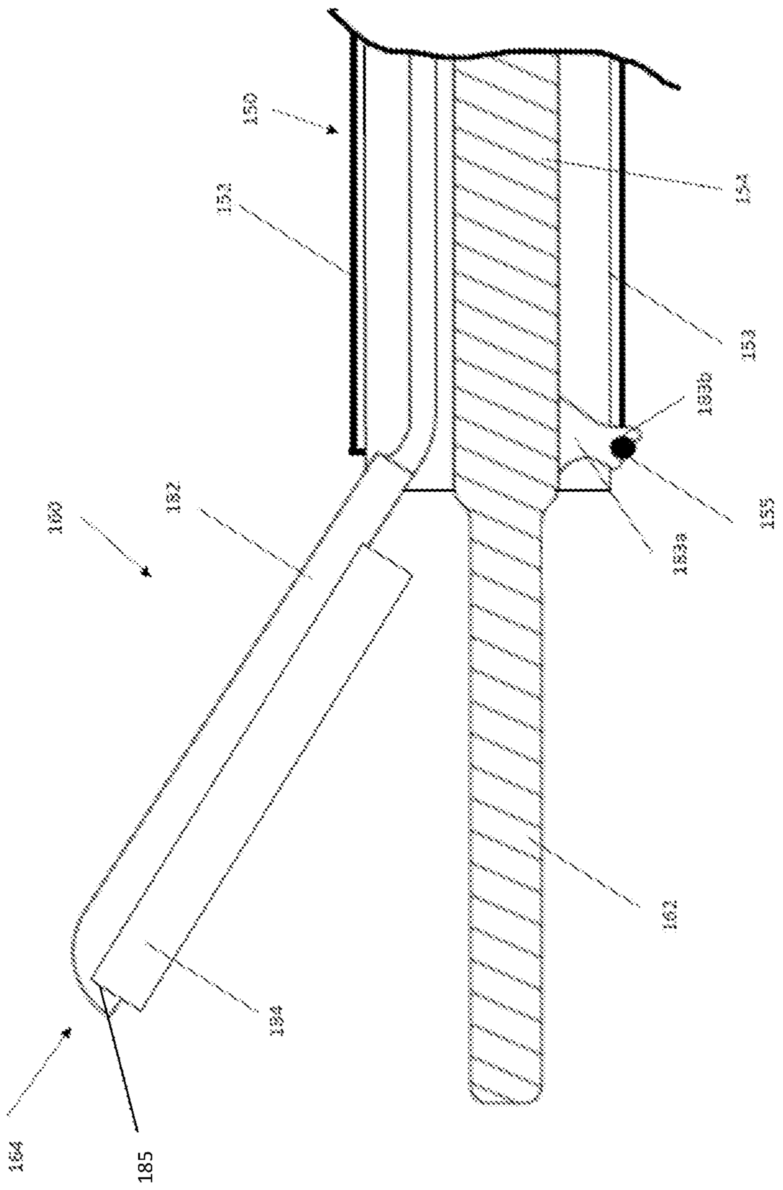
FIG. 5 is a longitudinal, cross-sectional view of a distal end portion of the surgical instrument of FIG. 1.

Waveguide 154, as noted above, extends from handle assembly 110 through inner sleeve 153 (FIG. 5). Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although non-conductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. In configurations where surgical instrument 100 is only configured for ultrasonic operation, electrosurgical plug 196 and associated components are omitted.

Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, and where electrosurgical functionality is provided, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that bipolar electrosurgical energy may be conducted between blade 162 and jaw member 164 (and/or between different portions of jaw member 164). In monopolar configurations, a second electrical lead wire 199 is electrically coupled to waveguide 154 such that monopolar electrosurgical energy may be supplied to tissue from blade 162. Alternatively or additionally, a second electrical lead wire 199 may electrically couple to jaw member 164 in the monopolar configuration to enable monopolar electrosurgical energy to be supplied to tissue from jaw member 164. In configurations where both bipolar and monopolar functionality are enabled, one or more of the second electrical lead wires 199 may be used for both the delivery of bipolar energy and monopolar energy; alternatively, bipolar and monopolar energy delivery may be provided by separate second electrical lead wires 199. One or more other second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode.

Figure 2:
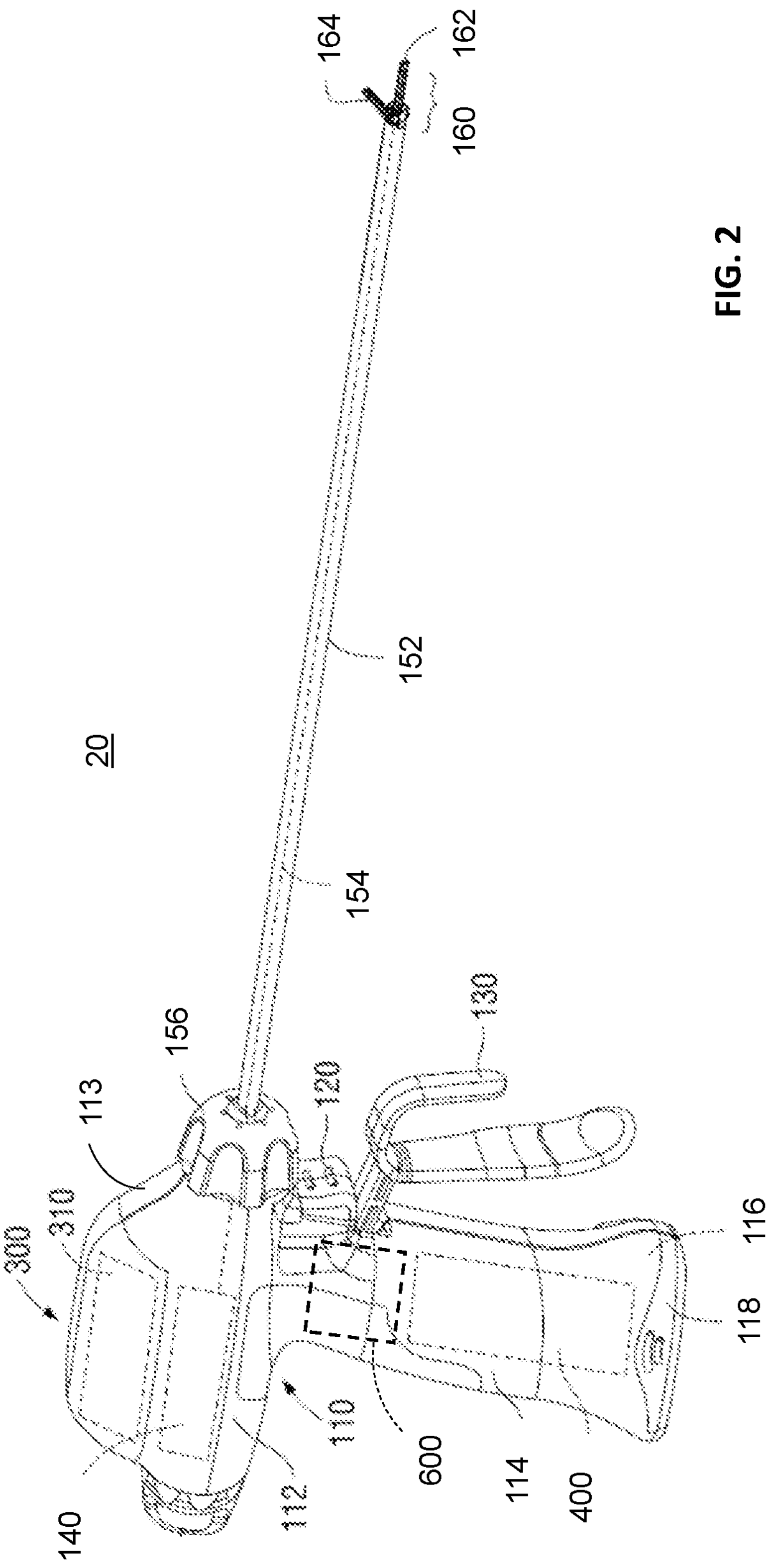
FIG. 2 is perspective view of another surgical system provided in accordance with the present disclosure including a surgical instrument incorporating an ultrasonic generator, electrosurgical generator, and power source therein.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated. More specifically, with reference to FIG. 2, another surgical system in accordance with the present disclosure is shown illustrated as a surgical instrument 20 supporting an ultrasonic generator 310, a power source (e.g., battery assembly 400), and an electrosurgical generator 600 thereon or therein. Surgical instrument 20 is similar to surgical instrument 100 (FIG. 1) and may include any of the features thereof except as explicitly contradicted below. Accordingly, only differences between surgical instrument 20 and surgical instrument 100 (FIG. 1) are described in detail below while similarities are omitted or summarily described.

Housing 112 of surgical instrument 20 includes a body portion 113 and a fixed handle portion 114 depending from body portion 113. Body portion 113 of housing 112 is configured to support an ultrasonic transducer and generator assembly ("TAG") 300 including ultrasonic generator 310 and ultrasonic transducer 140. TAG 300 may be permanently engaged with body portion 113 of housing 112 or removable therefrom.

Fixed handle portion 114 of housing 112 defines a compartment 116 configured to receive battery assembly 400 and electrosurgical generator 600 and a door 118 configured to enclose compartment 116. An electrical connection assembly (not shown) is disposed within housing 112 and serves to electrically couple activation button 120, ultrasonic generator 310 of TAG 300, and battery assembly 400 with one another when TAG 300 is supported on or in body portion 113 of housing 112 and battery assembly 400 is disposed within compartment 116 of fixed handle portion 114 of housing 112, thus enabling activation of surgical instrument 20 in an ultrasonic mode in response to appropriate actuation of activation button 120. Further, the electrical connection assembly or a different electrical connection assembly disposed within housing 112 serves to electrically couple activation button 120, electrosurgical generator 600, battery assembly 400, and end effector assembly 160 (e.g., blade 162 and jaw member 164 and/or different portions of jaw member 164) with one another when electrosurgical generator 600 and battery assembly 400 are disposed within compartment 116 of fixed handle portion 114 of housing 112, thus enabling activation of surgical instrument 20 in an electrosurgical mode, e.g., bipolar RF, in response to appropriate actuation of activation button 120. For a monopolar electrosurgical mode, return electrode device 500 (FIG. 1) may be configured to connect to surgical instrument 20 (electrosurgical generator 600 thereof, more specifically), to complete a monopolar circuit through tissue and between surgical instrument 30 (e.g., blade 162 and/or jaw member 164) and return electrode device 500 (FIG. 1).

Figure 3A:
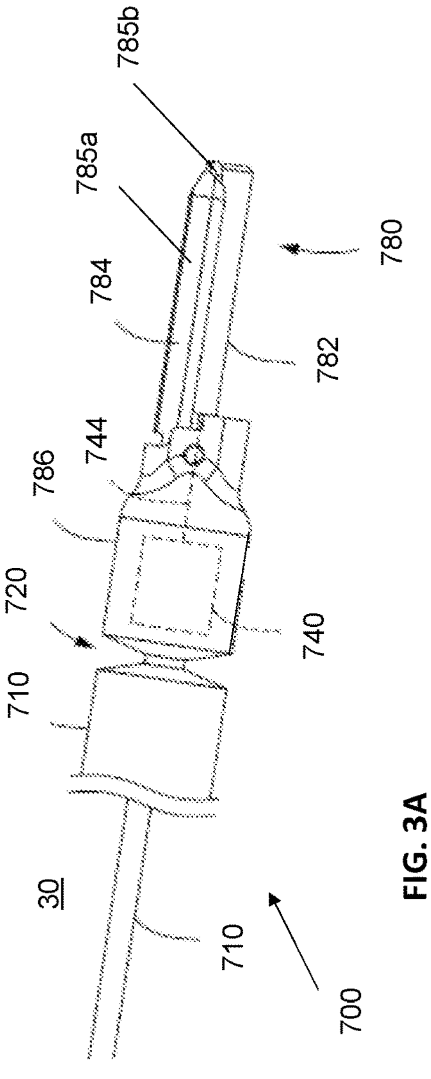
FIGS. 3A and 3B are perspective views of a distal portion of still another surgical instrument provided in accordance with the present disclosure with a distal end portion thereof enlarged and an end effector assembly thereof disposed in un-articulated and articulated positions, respectively.
Figure 3B:
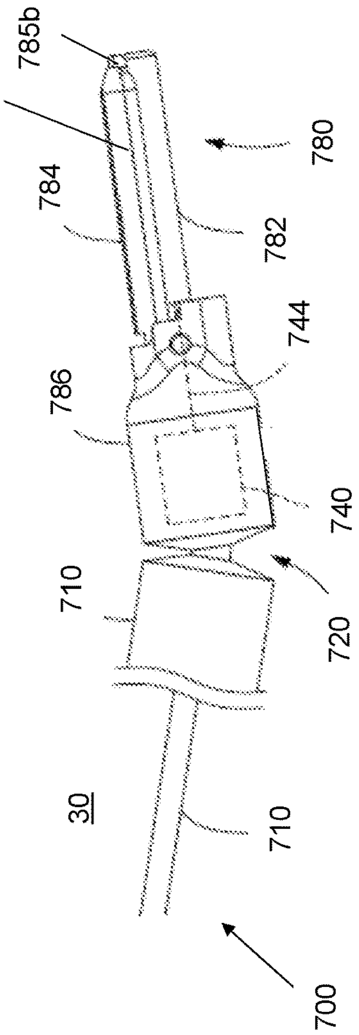

With reference to FIGS. 3A and 3B, a distal portion of another surgical instrument 30 provided in accordance with the present disclosure is shown. Surgical instrument 30 may be configured similar to and include any of the features of surgical instrument 100 (for use with a remote generator 200 as part of system 10) (FIG. 1) or surgical instrument 20 (including ultrasonic and electrosurgical generators 310, 600 and a battery assembly 400 thereon or therein) (FIG. 2), except as explicitly contradicted below. Accordingly, only differences between surgical instrument 30 and surgical instruments 100, 20 (FIGS. 1 and 2, respectively) are described in detail below while similarities are omitted or summarily described.

Surgical instrument 30 includes a housing (not shown, for manual manipulation or attachment to a surgical robot) and an elongated assembly 700 extending distally from the housing. Elongated assembly 700 of surgical instrument 30 includes an elongated shaft 710 having one or more articulating portions 720, an ultrasonic transducer 740, and an end effector assembly 780 including a blade 782, a jaw member 784, and a distal housing 786.

Elongated shaft 710, as noted above, extends distally from the housing. The one or more articulating portions 720 are disposed along at least a portion of elongated shaft 710. More specifically, an articulating portion 720 is shown in FIGS. 3A and 3B in the form of an articulating joint disposed at a distal end portion of elongated shaft 710 and coupled to distal housing 786 of end effector assembly 780 such that articulation of articulating portion 720 relative to a longitudinal axis of elongated shaft 710 articulates end effector assembly 780 relative to the longitudinal axis of elongated shaft 710. However, it is also contemplated that additional or alternative articulating portions may be disposed along some or all of elongated shaft 710 periodically, intermittently, or continuously (for a portion or the entirety of elongated shaft 710). Each articulating portion 720 may include one or more articulation joints, linkages, flexible portions, malleable portions, and/or other suitable articulating structures to enable articulation of end effector assembly 780 relative to the longitudinal axis of elongated shaft 710 in at least one direction, e.g., pitch articulation and/or yaw articulation. In configurations, the one or more articulating portions 720 are configured to enable both pitch articulation and yaw articulation; in other configurations, unlimited articulation in any direction is enabled.

Jaw member 784 is pivotably mounted on and extends distally from distal housing 786. A drive assembly (not shown) of surgical instrument 30 operably couples the actuator, e.g., clamp trigger 130 (FIG. 1), with jaw member 784 of end effector assembly 780 by way of a jaw drive (not shown) such that the actuator is selectively actuatable to pivot jaw member 784 relative to distal housing 786 and blade 782 of end effector assembly 780 from an open position to a clamping position for clamping tissue between jaw member 784 and blade 782. The jaw drive may include one or more drive shafts, drive sleeves, drive cables, gears, cams, and/or other suitable components. Jaw member 784 includes a more-rigid structural body 785*a*, which is pivotably mounted on a distal end portion of distal housing 786, and a more-compliant jaw liner 785*b*, which is captured by the more-rigid structural body 785*b* and positioned to oppose blade 782 to enable clamping of tissue therebetween.

In configurations where surgical instrument 30 also includes electrosurgical functionality (e.g., bipolar RF and/or monopolar RF), electrical lead wires (not shown) extend through elongated shaft 710 and articulating portion 720 to electrically coupled to ultrasonic horn 744 or blade 782, and/or to jaw member 784 such that bipolar electrosurgical energy may be conducted between blade 782 and jaw member 784 (and/or between different portions of jaw member 784) and/or such that monopolar electrosurgical energy may be supplied to tissue from blade 782 and/or jaw member 784.

An articulation assembly (not shown) including gears, pulleys, sleeves, cables, etc. operably couples a proximal articulation actuator (not shown) with articulating portion 720 such that actuation of the proximal articulation actuator manipulates articulating portion 720 to thereby articulate end effector assembly 780 relative to the longitudinal axis of elongated shaft 710.

Continuing with reference to FIGS. 3A and 3B, an ultrasonic transducer 740 is disposed within distal housing 786 and positioned distally of articulating portion 720, an ultrasonic horn 744 extends distally from ultrasonic transducer 740, and blade 782 extends distally from ultrasonic horn 744. Thus, in contrast to surgical instruments 100, 20 (FIGS. 1 and 2, respectively), ultrasonic transducer 740 is disposed within distal housing 786 distally of articulating portion 720 rather than proximally in the housing of the instrument. Alternatively, ultrasonic transducer 740 may be positioned proximally of articulating portion 720 (in the housing or otherwise positioned), and a waveguide (not shown) including one or more articulating portions, e.g., flexible portions, joint portions, linkage portions, etc., may extend through articulating portion 720 and interconnect ultrasonic transducer 740 with blade 782 such that ultrasonic energy produced by ultrasonic transducer 740 can be transmitted along the waveguide to blade 782 regardless of the articulation of articulating portion 720.

In some configurations, distal housing 786, including ultrasonic transducer 740 therein, defines an outer diameter less than about 15 mm, less than about 12 mm, less than about 10 mm, less than about 8 mm, less than about 5 mm, or less than about 3 mm. As such, ultrasonic transducer 740, in such configurations, may define a sufficiently small diameter (for example, 10% less than the diameters above) so as to enable operable receipt within distal housings 786 of the above-noted dimensions, respectively. By providing a configuration with the above-noted outer diameters, surgical instrument 30 may be utilized minimally-invasively through standard sizes of access devices. Ultrasonic transducer 740, other than its overall size, may be configured similar to ultrasonic transducer 140 (FIG. 1) or any other suitable ultrasonic transducer. For example, ultrasonic transducer 740 may include a stack of piezoelectric elements secured, under pre-compression between a proximal end mass and ultrasonic horn 744 with first and second electrodes electrically coupled between piezoelectric elements of the stack of piezoelectric elements to enable energization thereof to produce ultrasonic energy. Electrical lead wires (not shown) connect the electrodes of ultrasonic transducer 740 with an ultrasonic generator (not shown) to enable an electrical drive signal generated by the ultrasonic generator to be imparted to the stack of piezoelectric elements of ultrasonic transducer 740 to energize the stack of piezoelectric elements to produce ultrasonic energy for transmission to blade 782 via ultrasonic horn 744.

Figure 4:
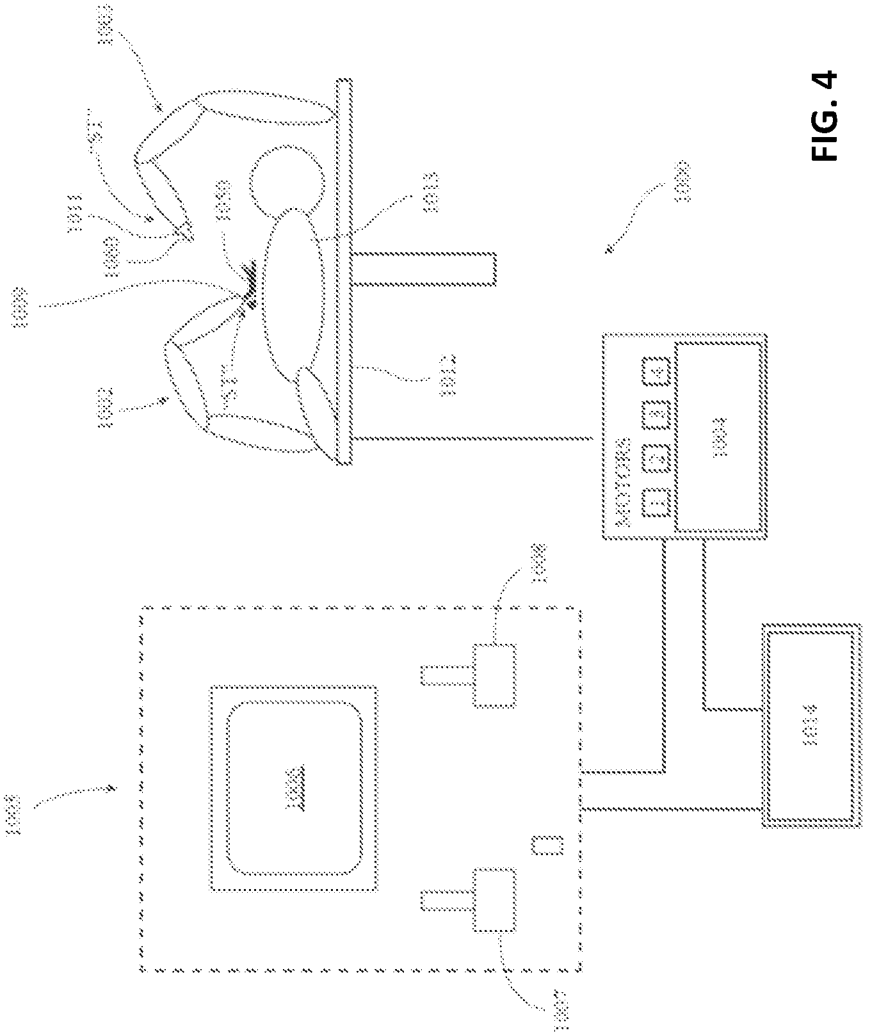
FIG. 4 is a schematic illustration of a robotic surgical system provided in accordance with the present disclosure.

Turning to FIG. 4, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be surgical instrument 100 (FIG. 1), surgical instrument 20 (FIG. 2), or surgical instrument 30 (FIGS. 3A and 3B), e.g., configured for use in both an ultrasonic mode and one or more electrosurgical (bipolar and/or monopolar) modes, wherein manual actuation features, e.g., actuation button 120 (FIG. 1), clamp lever 130 (FIG. 1), the proximal articulation actuator, etc., are replaced with robotic inputs. In such configurations, robotic surgical system 1000 may include or be configured to connect to an ultrasonic generator, an electrosurgical generator, and/or a power source. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 7:
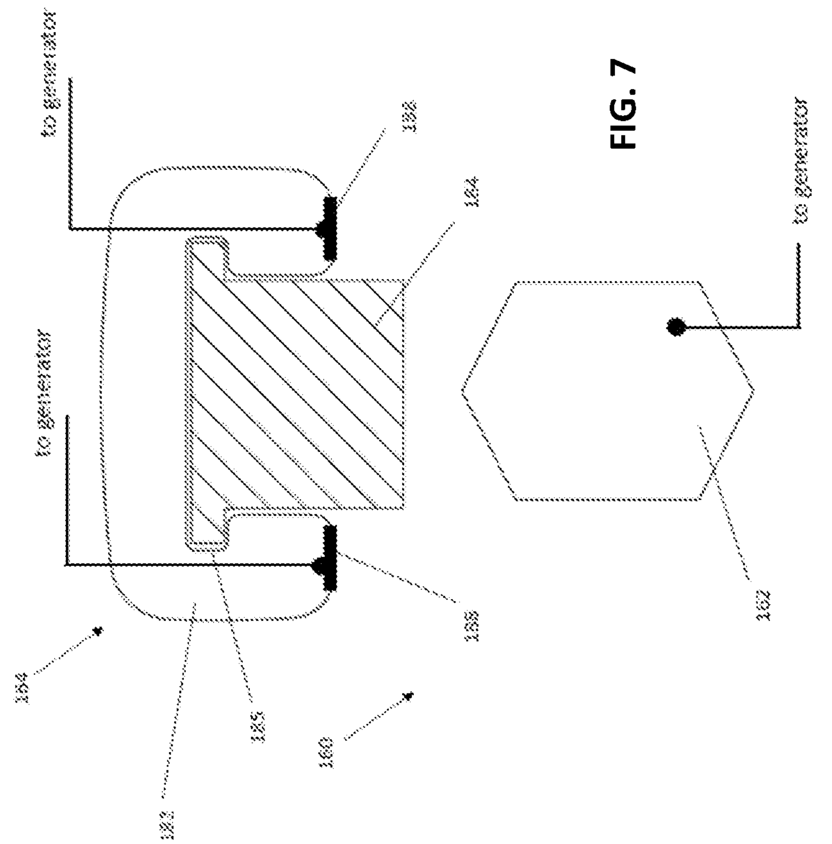
FIG. 7 is a transverse, cross-sectional view of another configuration of the end effector assembly of the surgical instrument of FIG. 1.
Figure 6:
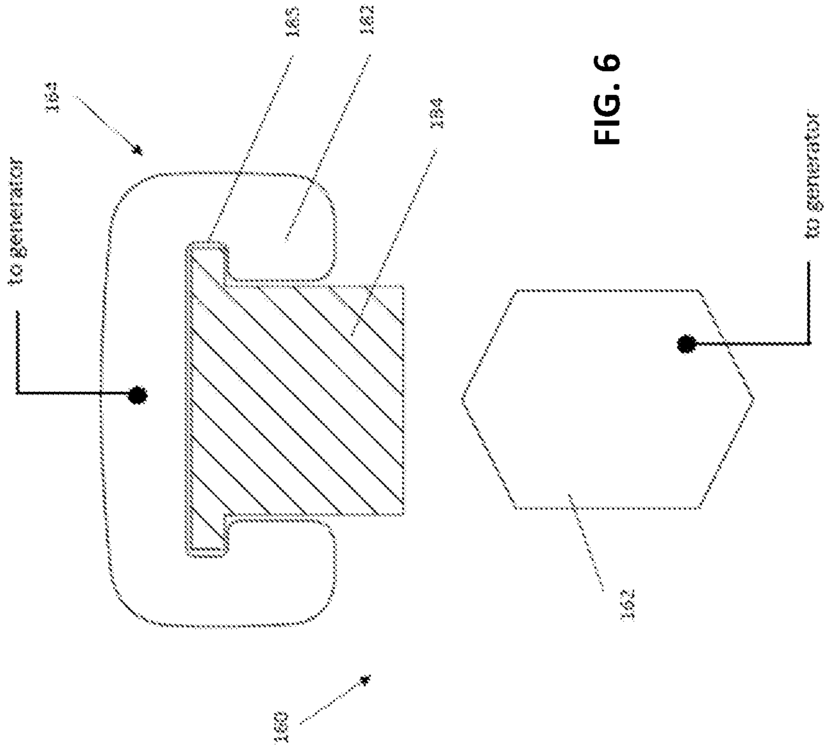
FIG. 6 is a transverse, cross-sectional view of the end effector assembly of the surgical instrument of FIG. 1.

Referring to FIGS. 5-7, end effector assembly 160 of surgical instrument 100 of surgical system 10 (FIG. 1) is detailed, although the aspects and features of end effector assembly 160 may similarly apply, to the extent consistent, to surgical instrument 20 (FIG. 2), surgical instrument 30 (FIGS. 3A and 3B), and/or any other suitable surgical instrument or system. End effector assembly 160, as noted above, includes blade 162 and jaw member 164. Blade 162 may define a linear configuration, may define a curved configuration, or may define any other suitable configuration, e.g., straight and/or curved surfaces, portions, and/or sections; one or more convex and/or concave surfaces, portions, and/or sections; etc. With respect to curved configurations, blade 162, more specifically, may be curved in any direction relative to jaw member 164, for example, such that the distal tip of blade 162 is curved towards jaw member 164, away from jaw member 164, or laterally (in either direction) relative to jaw member 164. Further, blade 162 may be formed to include multiple curves in similar directions, multiple curves in different directions within a single plane, and/or multiple curves in different directions in different planes. In addition, blade 162 may additionally or alternatively be formed to include any suitable features, e.g., a tapered configuration, various different cross-sectional configurations along its length, cut outs, indents, edges, protrusions, straight surfaces, curved surfaces, angled surfaces, wide edges, narrow edges, and/or other features.

Blade 162 may define a polygonal, rounded polygonal, or any other suitable cross-sectional configuration(s). Waveguide 154 or at least the portion of waveguide 154 proximally adjacent blade 162, may define a cylindrical shaped configuration. Plural tapered surfaces (not shown) may interconnect the cylindrically shaped waveguide 154 with the polygonal (rounded edge polygonal, or other suitable shape) configuration of blade 162 to define smooth transitions between the body of waveguide 154 and blade 162.

Blade 162 may be wholly or selectively coated with a suitable material, e.g., a non-stick material, an electrically insulative material, an electrically conductive material, combinations thereof, etc. Suitable coatings and/or methods of applying coatings include but are not limited to Teflon®, polyphenylene oxide (PPO), deposited liquid ceramic insulative coatings; thermally sprayed coatings, e.g., thermally sprayed ceramic; Plasma Electrolytic Oxidation (PEO) coatings; anodization coatings; sputtered coatings, e.g., silica; ElectroBond® coating available from Surface Solutions Group of Chicago, IL, USA; or other suitable coatings and/or methods of applying coatings.

Continuing with reference to FIGS. 5-7, blade 162, as noted above, in addition to receiving ultrasonic energy transmitted along waveguide 154 from ultrasonic transducer 140 (FIG. 1), is adapted to connect to generator 200 (FIG. 1) to enable the supply of RF energy to blade 162 for conduction to tissue in contact therewith. In bipolar configurations, RF energy is conducted between blade 162 and jaw member 164 (or between portions of jaw member 164 and/or blade 162) and through tissue disposed therebetween to treat tissue. In monopolar configurations, RF energy is conducted from blade 162, serving as the active electrode, to tissue in contact therewith and is ultimately returned to generator 200 (FIG. 1) via return electrode device 500 (FIG. 1), serving as the passive or return electrode.

Jaw member 164 of end effector assembly 160 includes more rigid structural body 182 and more compliant jaw liner 184. Structural body 182 may be formed from an electrically conductive material, e.g., stainless steel, and/or may include electrically conductive portions. Structural body 182 includes a pair of proximal flanges 183*a* that are pivotably coupled to the inner support sleeve 153 via receipt of pivot bosses (not shown) of proximal flanges 183*a* within corresponding openings (not shown) defined within the inner support sleeve 153 and operably coupled with outer drive sleeve 152 via a drive pin 155 secured relative to outer drive sleeve 152 and pivotably received within apertures 183*b* defined within proximal flanges 183*a*. As such, sliding of outer drive sleeve 152 about inner support sleeve 153 pivots jaw member 164 relative to blade 162 from a spaced apart position to an approximated position to clamp tissue between jaw liner 184 of jaw member 164 and blade 162.

With reference to FIG. 6, structural body 182 may be adapted to connect to a source of electrosurgical energy, e.g., generator 200 (FIG. 1), and, in a bipolar electrosurgical mode, is charged to a different potential as compared to blade 162 to enable the conduction of bipolar electrosurgical (e.g., RF) energy through tissue clamped therebetween, to treat the tissue. In a monopolar electrosurgical mode, structural body 182 may be un-energized, may be charged to the same potential as compared to blade 162 (thus both defining the active electrode), or may be energized while blade 162 is not energized (wherein structural body 182 defines the active electrode). In either monopolar configuration, energy is returned to generator 200 (FIG. 1) via return electrode device 500 (FIG. 1), which serves as the passive or return electrode.

Referring to FIG. 7, as an alternative to the entirety of structural body 182 of jaw member 164 being connected to generator 200 (FIG. 1), the structural body may be formed from or embedded at least partially in an insulative material, e.g., an overmolded plastic. In such configurations, electrically conductive surfaces 188, e.g., in the form of plates, may be disposed on or captured by the overmolded plastic to define electrodes on either side of jaw liner 184 on the blade facing side of jaw member 164. The electrically conductive surfaces 188, in such aspects, are connected to generator 200 (FIG. 1) and may be energized for use in bipolar and/or monopolar configurations, e.g., energized to the same potential as one another and/or blade 162 and/or different potentials as one another and/or blade 162. In aspects, electrically conductive surfaces 188 are disposed at additional or alternative locations on jaw member 164, e.g., along either or both sides thereof, along a back surface thereof, etc.

Again referring to FIGS. 5-7, jaw liner 184 is shaped complementary to a cavity 185 defined within structural body 182, e.g., defining a T-shaped configuration, to facilitate receipt and retention therein, although other configurations are also contemplated. Jaw liner 184 is fabricated from an electrically insulative, compliant material such as, for example, polytetrafluoroethylene (PTFE). The compliance of jaw liner 184 enables blade 162 to vibrate while in contact with jaw liner 184 without damaging components of ultrasonic surgical instrument 100 (FIG. 1) and without compromising the hold on tissue clamped between jaw member 164 and blade 162. Jaw liner 184 extends from structural body 182 towards blade 162 to inhibit contact between structural body 182 and blade 162 in the approximated position of jaw member 164. The insulation of jaw liner 184 maintains electrical isolation between blade 162 and structural body 182 of jaw member 164, thereby inhibiting shorting.

Figure 8A:
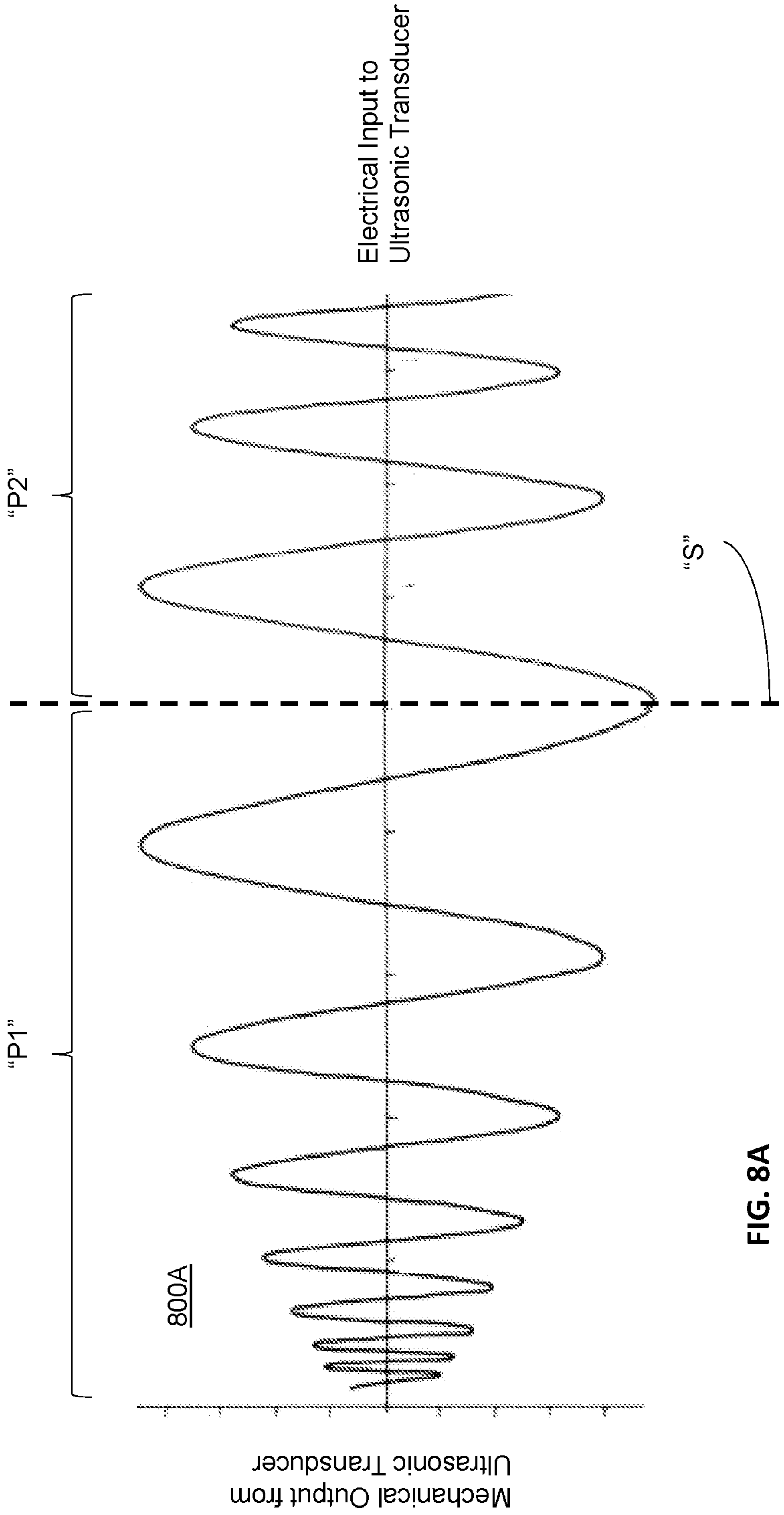
FIG. 8A is an exemplary graph representing the mechanical output from an ultrasonic transducer as a function of the electrical input to the ultrasonic transducer.
Figure 8B:
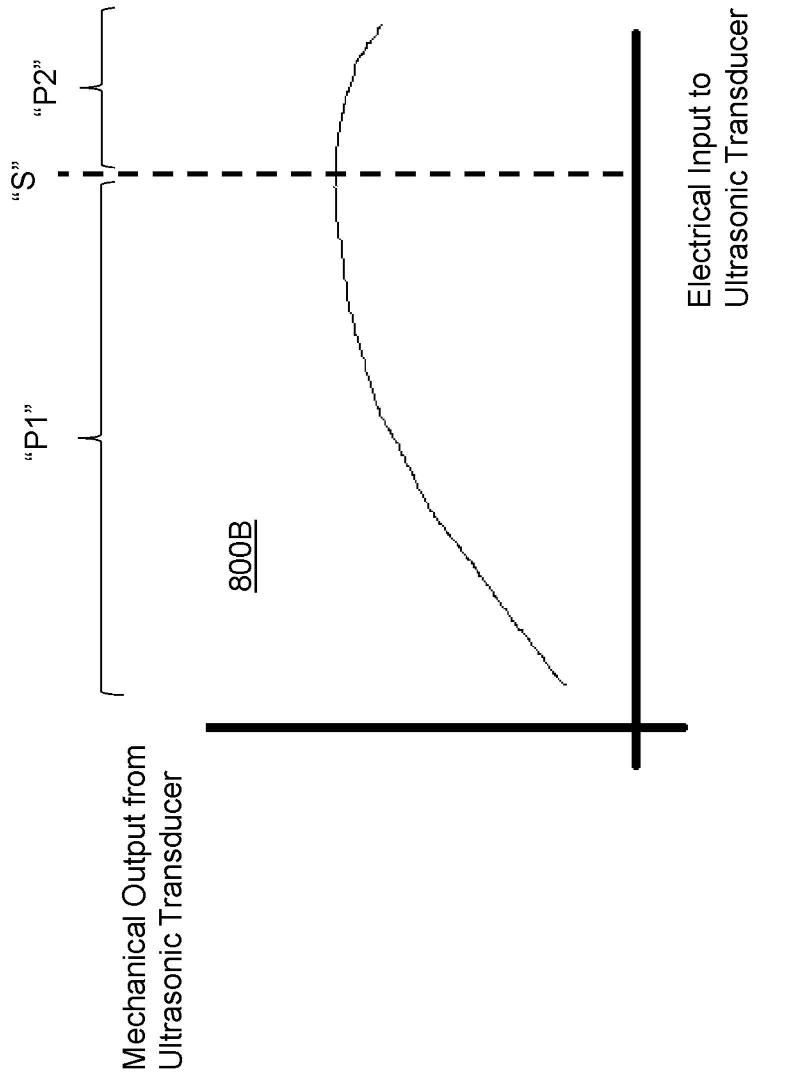
FIG. 8B is another exemplary graph representing the magnitude of mechanical output from an ultrasonic transducer as a function of the electrical input to the ultrasonic transducer.

Turning to FIGS. 8A and 8B, exemplary graphs 800A, 800B representing the mechanical output and magnitude of mechanical output, respectively, of an ultrasonic transducer (e.g., ultrasonic transducer 140 (FIG. 1), ultrasonic transducer 740 (FIGS. 3A and 3B), and/or any other suitable ultrasonic transducer of a surgical instrument or system) as a function of the electrical input to the ultrasonic transducer is shown. It is noted that graphs 800A, 800B are exemplary in that they are provided to illustrate general trends and may not match the relationship between the mechanical output from the ultrasonic transducer and the electrical input to the ultrasonic transducer for any given ultrasonic transducer and/or may not match the specific numerical values for the input and/or output. It is contemplated that the input may be power (watts), or any other suitable representation of the electrical input to an ultrasonic transducer (e.g., voltage (volts), current (amps), etc.). The output may be displacement (meters) or any other suitable representation of the mechanical output of an ultrasonic transducer (e.g., velocity (m/s) (provided as a Root Mean Square (RMS) velocity, for example), acceleration ($m/s^2$), force (N), stress (Pa), strain (m/m), or power (W)). The output displacement (or other output measurement) may be measured at a reference point of the ultrasonic transducer or other reference point, e.g., at a distal tip of blade 162 (FIGS. 1 and 5-7).

Continuing with reference to FIGS. 8A and 8B, it is generally understood that as the electrical input to an ultrasonic transducer is increased, the mechanical output by the ultrasonic transducer is increased. However, it has been found that this general principle holds true only for a first period "P1" and that, at a threshold where the ultrasonic transducer is saturated, referred to herein as the saturation point "S" of the ultrasonic transducer, further increase in the electrical input to the ultrasonic transducer no longer results in increased mechanical output by the ultrasonic transducer. That is, once the saturation point "S" of the ultrasonic transducer is reached, the mechanical output by the ultrasonic transducer levels off and/or decreases in response to increased electrical input, e.g., in second period "P2." Continued increase in electrical input once the saturation point "S" has been reached, e.g., in second period "P2," could also lead to over-stress and/or damage to the ultrasonic transducer.

The particular saturation point "S" of an ultrasonic transducer may depend on static factors, e.g., the configuration (size, materials, construction, assembly, etc.) of the ultrasonic transducer, and/or dynamic factors, e.g., impedance of the ultrasonic transducer, the load on the transducer (or blade coupled thereto), the temperature of the transducer (or blade coupled thereto), operating parameters, etc. The behavior of the ultrasonic transducer, e.g., the mechanical output produced thereby, at and/or after reaching the saturation point "S," e.g., the behavior of the ultrasonic transducer in period "P2," may likewise depend on static and/or dynamic factors.

The present disclosure leverages the above-noted findings of an ultrasonic transducer saturation point "S" to facilitate design, feedback, and/or control of ultrasonic transducers and/or surgical systems. More specifically, the saturation point "S" of an ultrasonic transducer can be leveraged in a variety of ways such as, for example: ultrasonic transducer and/or surgical instrument design can be guided by the saturation point "S" to maximize efficiency, minimize size, minimize power consumption, etc. and/or to maximize the saturation point "S;" the saturation point "S" of an ultrasonic transducer can be monitored to provide feedback such as, for example, load sensing (e.g., to detect matter and properties thereof in contact with the blade coupled to the ultrasonic transducer), temperature sensing, etc.; and/or the saturation point "S" may be utilized to facilitate control of the ultrasonic transducer such as, for example, to enable operation of the ultrasonic transducer at or close to the saturation point "S" and, thus, at or close to providing the maximum output thereof.

With regard to ultrasonic transducer and surgical instrument design, more specifically, the required maximum mechanical output of an ultrasonic transducer can be utilized together with the saturation point "S" in order to design an ultrasonic transducer that is capable of providing the requisite maximum mechanical output in a minimal package, e.g., minimizing volume, cross-sectional diameter, and/or other dimensions of the ultrasonic transducer; and/or minimizing power consumption by the ultrasonic transducer, e.g., by providing a smaller ultrasonic transducer and/or an ultrasonic transducer with reduced power loss. Additionally or alternatively, design, assembly, material, and/or other features may be taken into consideration in order to maximize the saturation point "S" of a particular size or other configuration of ultrasonic transducer, thus enabling an increase in the maximum mechanical output of the ultrasonic transducer without requiring an increased size (and/or power consumption).

Figure 9:
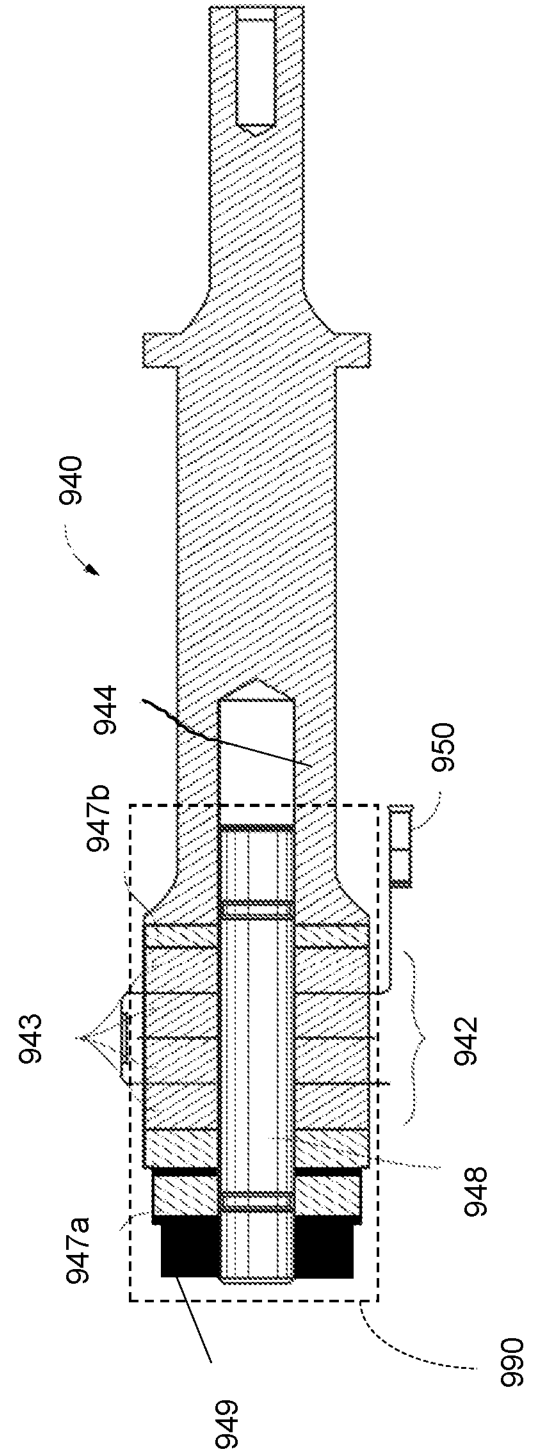
FIG. 9 is a longitudinal, cross-sectional of an ultrasonic transducer provided in accordance with the present disclosure and configured for use with the surgical systems of FIGS. 1-4 or any other suitable surgical system.

Referring to FIG. 9, in conjunction with FIGS. 8A and 8B, an exemplary ultrasonic transducer 940 is provided which may be used as ultrasonic transducer 140 (FIGS. 1 and 2), ultrasonic transducer 740 (FIGS. 3A and 3B), or the ultrasonic transducer of any other suitable surgical instrument. Ultrasonic transducer 940 include a piezoelectric stack 942, ultrasonic horn 944, a proximal end mass 947*a*, in some aspects a distal end mass 947*b* (although in other aspects distal end mass 947*b* is excluded), and a rod 948 securing piezoelectric stack 942 between proximal and distal end masses 947*a*, 947*b*, respectively, and to horn 944 under compression. Rod 948 may be secured via a proximal nut 949 threaded or otherwise engaged about rod 948 at a proximal end portion thereof and may be secured distally within a cavity defined within horn 944 via welding, threaded engagement, or in any other suitable manner. The pre-compression of piezoelectric stack 942 against horn 944 (directly or indirectly), enables efficient and effective transmission of ultrasonic energy from piezoelectric stack 942 to horn 944 for transmission along a waveguide to a blade (see FIGS. 1, 2, and 5, for example) or directly from horn 944 to a blade (see FIGS. 3A and 3B, for example). In some configurations, distal end mass 947*a* is omitted and horn 944 acts as the distal end mass against which piezoelectric stack 942 is directly compressed.

Ultrasonic transducer 940 further includes electrode assembly 950 (partially shown in FIG. 9) having at least one electrode disposed in contact with a surface of at least one piezoelectric element 943 of piezoelectric stack 942 and at least one electrode disposed in contact with an opposed surface of the at least one piezoelectric element 943 of piezoelectric stack 942 to, as noted above, enable an electrical input drive signal, e.g., a drive signal voltage, to be applied across piezoelectric stack 942.

Ultrasonic transducer 940 can be designed such that the requisite maximum mechanical output required of ultrasonic transducer 940 is achieved at substantially the saturation point "S;" in other words, such that ultrasonic transducer 940 operates substantially at its maximum to achieve the required maximum mechanical output to drive the blade (or other component) of the surgical instrument including ultrasonic transducer 940. By designing ultrasonic transducer 940 in this manner, the size and/or power consumption of ultrasonic transducer 940 can be minimized, as the ultrasonic transducer 940 would not have additional size and/or consume additional power to support unnecessary and unused additional capacity.

With respect to a minimum size of ultrasonic transducer 940, where size is a design constraint, it is contemplated that the saturation point "S" may be leveraged (and/or modified as detailed herein or in any other suitable manner) to provide an ultrasonic transducer 940 that operates at substantially the saturation point "S" (in the maximum output mode thereof) to drive the blade (or other component) of the surgical instrument including ultrasonic transducer 940 at a suitable maximum mechanical output (in terms of blade velocity). The maximum mechanical output may be, in aspects at least 6.0 m/s RMS; in other aspects at least 8.0 m/s RMS; and in still other aspects at least 10.0 m/s RMS. This may be achieved, for example, with e ultrasonic transducer 940 defining a maximum outer diameter of, in aspects no greater than 12 mm; in other aspects no greater than 10 mm; and in still other aspects no greater than 8 mm.

Continuing with reference to FIGS. 8A-8B and 9, designing the ultrasonic transducer 940 to operate at substantially the saturation point "S" (in the maximum output mode thereof) may be sufficient to enable a suitably small size; in other aspects, the design of ultrasonic transducer 940 can be modified to increase the saturation point "S" and, thus, increase the maximum mechanical output thereof, and/or to increase the maximum mechanical output at the saturation point "S." For example, in aspects, a cooling system 990, e.g., including one or more passive cooling devices (such as heat sinks) and/or one or more active cooling devices (such as cooling fluid circulation systems, Peltier coolers, etc.), may be provided to reduce the temperature of piezoelectric elements 943 during operation.

In other aspects, the pre-compression of piezoelectric stack 942 between proximal and distal end masses 947*a*, 947*b* may be adjusted, e.g., by adjusting proximal nut 949 or in any other suitable manner, to modify the pre-stress on piezoelectric stack 942 to increase the saturation point "S" and/or the maximum mechanical output at the saturation point "S." The amount of pre-compression corresponding to the increased saturation point "S" and/or maximum mechanical output may be determined empirically or in any other suitable manner.

The material(s) forming the piezoelectric elements 943 may also be selected to increase the saturation point "S" and/or the maximum mechanical output without increasing a size, e.g., outer diameter, of the piezoelectric stack 942. Alternatively, or additionally, the diameter and/or width of some of the piezoelectric elements 943 may be modified relative to the diameter and/or width of the other piezoelectric elements 943 to increase the saturation point "S" and/or the maximum mechanical output. For example, a center element 943 or elements 943 may be larger than the end elements 943. In aspects, the interface between piezoelectric stack 942 (and/or distal end mass 947*b*) and ultrasonic horn 944 may be positioned at or near (e.g., within 10% of) a node point to potentially increase the saturation point "S" and/or the maximum mechanical output. As another example, the frequency of the input electrical drive signal may be increased to potentially increase the saturation point "S" and/or the maximum mechanical output. As still another example, the input electrical drive signal may be biased, e.g., with a DC offset, to potentially increase the saturation point "S" and/or the maximum mechanical output.

In still other configurations, ultrasonic transducer 940 may include plural independently-energizable piezoelectric stacks 942 and/or one or more piezoelectric stacks 942 with independently-energizable piezoelectric elements 943 or groups of piezoelectric elements 943. In such configurations, depending upon the required output and/or other conditions, a selection of the piezoelectric stack(s) 942 and/or piezoelectric element(s) 943 are activated and driven at substantially a saturation point "S" corresponding to the activated portion(s) of the ultrasonic transducer 940. As needed to provide a particular output, the piezoelectric stack(s) 942 and/or piezoelectric element(s) 943 that are activated may be increased, decreased, and/or switched and, correspondingly, the ultrasonic transducer 940 is then driven at substantially the saturation point "S" corresponding to the then-activated portion(s). In this manner, varied output and/or accommodation of varied conditions can be achieved while running ultrasonic transducer 940 substantially at its effective saturation point "S" (e.g., the saturation point "S" of the active portion(s) thereof).

In aspects, for example but not limited to where the ultrasonic transducer 940 at a given size and configured according to any of the aspects above and/or in any other suitable manner is still not capable of providing the requisite mechanical output to achieve a desired tissue treatment when running at substantially its saturation point "S," an electrosurgical mode of operation may be initiated in conjunction with the delivery of ultrasonic energy to facilitate the desired tissue treatment. The electrosurgical mode may be a bipolar RF mode, a monopolar RF mode, or a polyphasic RF mode in any of the configurations detailed above or in any other suitable configuration, and may be pulsed, continuous, or provided in any other suitable manner together with, alternatively with, overlapping with, etc., the ultrasonic energy to achieve a desired tissue treatment and/or to speed up the desired tissue treatment. The tissue treatment may be, for example, tissue sealing, tissue transection, etc.

Figure 10:
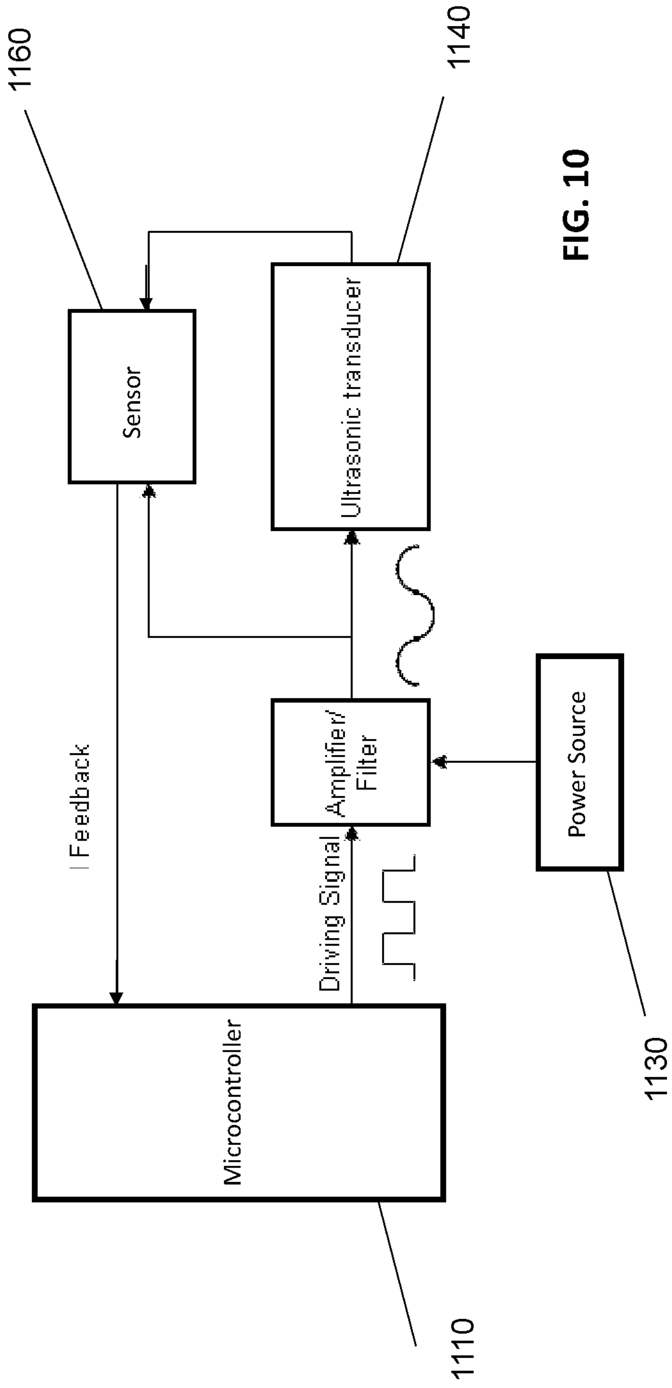
FIG. 10 is a simplified block diagram of one configuration of power and control signal communication between a generator and an ultrasonic transducer for use with the surgical systems of FIGS. 1-4 or any other suitable surgical system.

Referring to FIG. 10, in conjunction with FIGS. 8A and 8B, as noted above, the saturation point "S" of an ultrasonic transducer can be monitored to provide feedback such as, for example, load sensing (e.g., to detect matter and properties thereof in contact with the blade coupled to the ultrasonic transducer), temperature sensing, etc.; and/or the saturation point "S" may be utilized to facilitate control of the ultrasonic transducer such as, for example, to enable operation of the ultrasonic transducer at or close to the saturation point "S" and, thus, at or close to providing the maximum output thereof. FIG. 10 provides a simplified block diagram including a microcontroller 1110 (e.g., of generator 200 (FIG. 1), ultrasonic generator 310 (FIG. 2), or any other suitable generator) and a power source 1130 (e.g., generator 200 (FIG. 1), battery 400 (FIG. 2), or any other suitable power source) configured to control and power the electrical input to the ultrasonic transducer 1140. Further, one or more sensors 1160 may be provided to sense one or more properties of the electrical input drive signal, the ultrasonic transducer 1140, and/or the mechanical output from the ultrasonic transducer 1140, and to feedback the same to microcontroller 1110.

The one or more sensors 1160, more specifically, may include, for example, a motional bridge configured to sense a mechanical motion of the ultrasonic transducer 1140. The mechanical motion feedback provided by the motional bridge may be utilized with the electrical input drive signal to the ultrasonic transducer 1140 to enable determination and monitoring of the saturation point "S" of the ultrasonic transducer 1140. Monitoring the saturation point "S" of the ultrasonic transducer 1140 can be utilized for determining, for example, a load on the blade coupled to the ultrasonic transducer 1140. By monitoring the load on the blade based on the saturation point "S," it can be determined whether the blade is in contact with a hard object such as, for example, the structural jaw (where the jaw liner has worn away), a component of another surgical instrument, a staple or surgical clip, bone, etc. Appropriate feedback, e.g., a warning, can then be provided to the user indicating the same. Monitoring the saturation point "S" to determine a load on the blade may be accomplished itself or together with an impedance sensor (as one of sensors 1160) configured to sense a mechanical load impedance of ultrasonic transducer 1140.

Monitoring the saturation point "S" can also be utilized to estimate a temperature of the blade coupled to the ultrasonic transducer 1140, either alone or in combination with a temperature sensor (as one of sensors 1160) configured to sense a temperature of ultrasonic transducer 1140. Knowing the blade temperature may be utilized to provide appropriate feedback, e.g., a warning, indicating to the that the blade is hot, to automatically initiate blade cooling where so provided, etc.

Referring still to FIGS. 8A-8B and 10, with respect to controlling ultrasonic transducer 1140 to run at or close to the saturation point "S," it is advantageous to control without reducing output as a function of the control and without overshoot. One such control method is point tracking, referred to herein as saturation point tracking. For example, microcontroller 1110 may implement a perturb and observe algorithm, a form of saturation point tracking, to constantly or periodically check the operating power and/or saturation point "S" to ensure the input electrical signal drives the ultrasonic transducer 1140 substantially at the saturation point "S" and, thus, such that a maximum mechanical output is achieved. Another form of saturation point tracking that may be implemented by microcontroller 1110 is incremental conductance, where the derivative of the voltage and/or current input is utilized to predict where the saturation point will be and, thus, enabling predictive-based control. In additional or alternative aspects, microcontroller 1110 may monitor the saturation point "S" to inhibit overshoot, e.g., to inhibit the input electrical signal from driving the ultrasonic transducer 1140 beyond the saturation point "S;" microcontroller 1110 may implement chirp control; microcontroller 1110 may implement frequency sweeping; and/or any other suitable feedback or other based control may be provided.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An ultrasonic surgical system, comprising:

an ultrasonic generator configured to provide an electrical drive signal;

an ultrasonic transducer configured to receive the electrical drive signal and, in response thereto, to produce ultrasonic mechanical motion;

a sensor configured to sense the ultrasonic mechanical motion of the ultrasonic transducer, wherein the ultrasonic surgical system is configured to determine a saturation point of the ultrasonic transducer based at least in part on the sensed ultrasonic mechanical motion and the electrical drive signal; and a blade coupled to the ultrasonic transducer and configured to receive the ultrasonic mechanical motion from the ultrasonic transducer for treating tissue in contact therewith, wherein the ultrasonic generator is configured to drive the ultrasonic transducer substantially at the saturation point such that the ultrasonic mechanical motion produced by the ultrasonic transducer is substantially equal to a maximum ultrasonic mechanical motion of the ultrasonic transducer.

2. The ultrasonic surgical system according to claim 1, further comprising:

a housing; and an elongated assembly extending distally from the housing, wherein the blade is positioned at a distal end portion of the elongated assembly.

3. The ultrasonic surgical system according to claim 2, wherein the ultrasonic transducer is supported on or within the housing.

4. The ultrasonic surgical system according to claim 2, wherein the ultrasonic generator is supported on or within the housing.

5. The ultrasonic surgical system according to claim 2, wherein the ultrasonic transducer is supported within the elongated assembly at a position distally-spaced from the housing.

6. The ultrasonic surgical system according to claim 5, wherein the elongated assembly is configured to articulate about at least one articulation joint, and wherein the ultrasonic transducer is positioned distally of the at least one articulation joint.

7. The ultrasonic surgical system according to claim 1, further comprising an ultrasonic waveguide interconnecting the ultrasonic transducer with the blade.

8. The ultrasonic surgical system according to claim 1, further comprising a jaw member movable relative to the blade between a spaced-apart position and an approximated position for clamping tissue therebetween.

9. The ultrasonic surgical system according to claim 8, wherein at least one of the jaw member or the blade is configured to connect to a source of electrosurgical energy for communicating electrosurgical energy to tissue clamped between the blade and the jaw member.

10. An ultrasonic surgical system, comprising:

an ultrasonic transducer configured, in response to receiving an electrical drive signal to drive the ultrasonic transducer at substantially a saturation point, to produce a maximum ultrasonic mechanical motion; and a blade coupled to the ultrasonic transducer and configured to receive the maximum ultrasonic mechanical motion therefrom, the ultrasonic transducer configured such that the maximum ultrasonic mechanical motion moves the blade at a velocity of at least 8 m/s RMS for treating tissue in contact therewith, wherein the ultrasonic surgical system is configured to determine the saturation point based at least in part on a sensor output and the electrical drive signal.

11. The ultrasonic surgical system according to claim 10, further comprising an ultrasonic generator configured to provide the electrical drive signal to the ultrasonic transducer.

12. The ultrasonic surgical system according to claim 10, further comprising:

a housing; and an elongated assembly extending distally from the housing, wherein the blade is positioned at a distal end portion of the elongated assembly.

13. The ultrasonic surgical system according to claim 12, wherein the ultrasonic transducer is supported within the elongated assembly at a position distally-spaced from the housing.

14. The ultrasonic surgical system according to claim 13, wherein the elongated assembly is configured to articulate about at least one articulation joint, and wherein the ultrasonic transducer is positioned distally of the at least one articulation joint.

15. The ultrasonic surgical system according to claim 10, wherein a maximum outer diameter of the ultrasonic transducer is no greater than about 8 mm.

16. The ultrasonic surgical system according to claim 10, wherein the ultrasonic transducer is configured such that the maximum ultrasonic mechanical motion moves the blade at a velocity of at least 10 m/s RMS for treating tissue in contact therewith.

17. The ultrasonic surgical system according to claim 10, further comprising a jaw member movable relative to the blade between a spaced-apart position and an approximated position for clamping tissue therebetween.

18. The ultrasonic surgical system according to claim 17, wherein at least one of the jaw member or the blade is configured to connect to a source of electrosurgical energy for communicating electrosurgical energy to tissue clamped between the blade and the jaw member.

19. A method of operating an ultrasonic surgical system, comprising:

determining a saturation point of an ultrasonic transducer based on a sensed mechanical motion of the ultrasonic transducer and an electrical drive signal provided to the ultrasonic transducer;

determining a modified electrical drive signal to drive the ultrasonic transducer substantially at the saturation point; and providing the modified electrical drive signal to the ultrasonic transducer such that the ultrasonic transducer produces a maximum ultrasonic mechanical motion for transmission to a blade coupled to the ultrasonic transducer for treating tissue in contact therewith.

20. The method according to claim 19, further comprising controlling the modified electrical drive signal to maintain the ultrasonic transducer substantially at the saturation point.

* * * * *